US00PP09874P

United States Patent [19]

Lenz

[11] Patent Number: Plant 9,874

[45] Date of Patent: Apr. 29, 1997

[54] *POTENTILLA FRUTICOSA* PLANT NAMED 'PINK BEAUTY'

[75] Inventor: Louis M. Lenz, Winnipeg, Canada

[73] Assignee: University of Manitoba, Winnipeg, Canada

[21] Appl. No.: 563,891

[22] Filed: Nov. 21, 1995

[51] Int. Cl.[6] ..... A01H 5/00

[52] U.S. Cl. ..... Plt./54.1

[58] Field of Search ..... Plt./54.1

*Primary Examiner*—James R. Feyrer

*Attorney, Agent, or Firm*—Burns, Doane, Swecker & Mathis, L.L.P.

[57] ABSTRACT

A new and distinctive cultivar of Shrubby Potentilla, botanically known as *Potentilla fruticosa*, is provided. This cultivar can be distinguished from other Potentilla cultivars by its large clear semi-double deep pink flowers of long flowering duration, superior foliage quality, and plant growth habit. Attractive pink flowers commonly are exhibited from the summer until the time of frost. A medium-sized compact round and spreading plant having deep green foliage is formed that tends to hold its foliage well even at the base of the plant. The new cultivar is an attractive landscape plant that is suitable for growing in a wide range of climatic zones. Good plant performance is possible even under hot and dry growing conditions where other pink-flowering cultivars of the same species have tended to perform poorly.

2 Drawing Sheets

SUMMARY OF THE INVENTION

The present invention comprises a new and distinct cultivar of *Potentilla fruticosa* plant, and hereinafter is referred to by the cultivar name 'Pink Beauty'.

The new cultivar was the product of a planned breeding program which had the objective of a new *Potentilla fruticosa* cultivar having a novel and highly distinctive phenotype.

The breeding program which resulted in the new cultivar of the present invention was carried out during 1986 in a controlled environment at the Department of Plant Science, University of Manitoba, Winnipeg, Manitoba, Canada. Initially the 'Pink Whisper' cultivar (non-patented in the United States) was crossed with the 'Yellowbird' cultivar (non-patented in the United States), and the product of this cross was backcrossed to the 'Yellowbird' parent. The parentage of the new cultivar can be summarized as follows:

('Pink Whisper×'Yellowbird')×Yellowbird'.

The seeds resulting from the above pollination were sown and many small plantlets were obtained which was physically and biologically different from each other. Selective study during 1987 resulted in the identification of a single plant of the new cultivar that initially was designated No. 87133. Such new cultivar at the time of its selection was found to exhibit an outstanding combination of characteristics as discussed hereafter.

It was found that the new *Potentilla fruticosa* cultivar of the present invention:

(a) forms in profusion attractive deep pink flowers substantially continuously from summer until frost, (b) exhibits a medium-sized compact round and spreading growth habit that tends to hold its foliage well even at the base of the plant, (c) grows satisfactorily even under hot and dry growing conditions where other pink-flowered cultivars of the same species have tended to perform poorly, and (d) forms attractive dark green foliage.

When compared to the 'Pink Whisper' parent, the new 'Pink Beauty' cultivar generally exhibits blossoms having a deeper pink coloration (as illustrated). It is found that the exact flower coloration of the new cultivar may vary somewhat with the ambient temperature that is encountered during the bud formation. More specifically, the pink coloration tends to be more intense when cooler temperatures are encountered during the bud formation stage. However, even when bud formation occurs under high temperature conditions, the resulting pink coloration of the new cultivar is consistently superior to and more pronounced than that of the other pink-flowered cultivars, such as 'Pink Whisper' cultivar. The pink flower coloration of the new cultivar commonly remains relatively constant over the passage of time once opening has occurred. The deep pink flowers of the new cultivar can be readily distinguished from the yellow flowers of the 'Goldfinger' cultivar (non-patented in the United States).

It has been determined that the new cultivar continues to grow well in the hot prairie provinces of Canada and in the midwestern portion of the United States.

The new cultivar requires minimal care and can be grown to advantage as attractive ornamentation in the landscape in view of its stable combination of attractive and distinctive characteristics.

Asexual propagation of the new cultivar by softwood cuttings at (a) the University of Manitoba, Winnipeg, Manitoba, Canada, (b) Portage la Prarie, Manitoba, Canada, and (c) St. Paul Minn., U.S.A., has demonstrated that the characteristics of the new cultivar as described herein are firmly fixed and are retained through successive generations of asexual propagation.

'Pink Beauty' has not been observed under all possible environmental conditions to date. Accordingly, it is possible that the phenotype may vary somewhat with other variations in the environment.

BRIEF DESCRIPTION OF THE PHOTOGRAPHS

The accompanying photographs show in color as nearly true as it is reasonably possible to make the same in color illustrates of this character, mature five-year old plants, blossoms, and foliage of the new cultivar together with the blossoms and foliage of two other *Potentilla fruticosa* cultivars for comparative purposes. The photographs of FIGS. 1 to 3 were prepared during September, 1994 at Winnipeg, Manitoba, Canada. The photograph of FIG. 4 was prepared during September, 1995 at Portage la Prairie, Manitoba, Canada.

Figure 1:
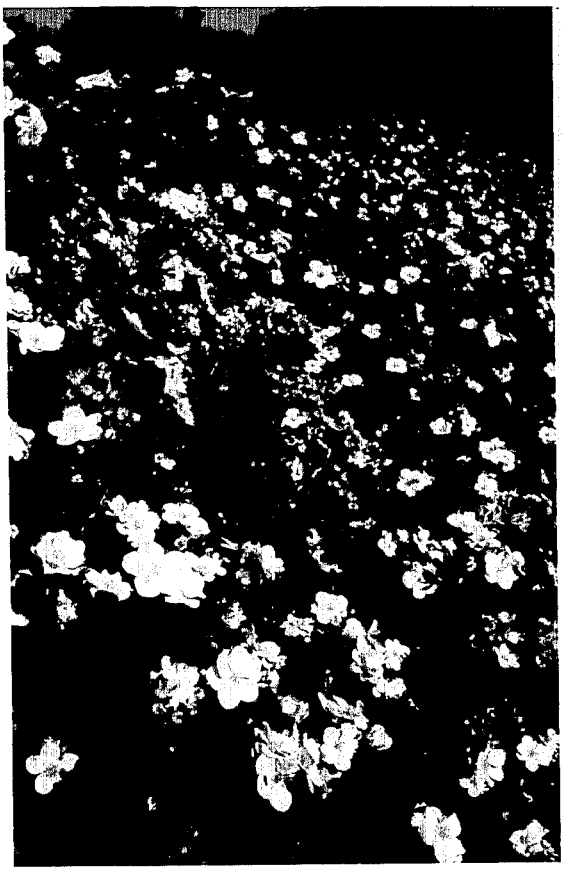
FIG. 1 illustrates a mass of flowering plants of the 'Pink Beauty' cultivar while growing in the field.
Figure 2:
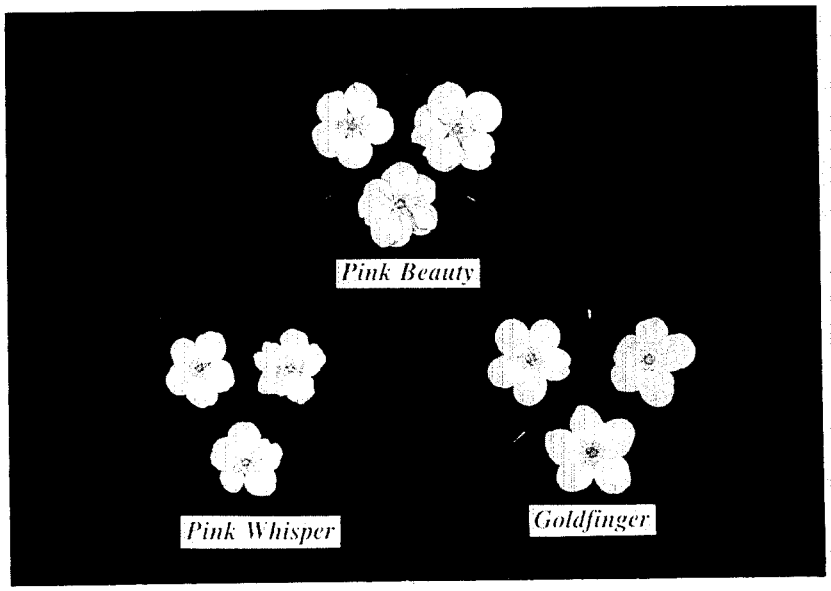
FIG. 2 illustrates for comparative purposes typical flowers of the 'Pink Beauty', 'Pink Whisper', and 'Goldfinger' cultivars of *Potentilla fruticosa* when removed from the plant.
Figure 3:
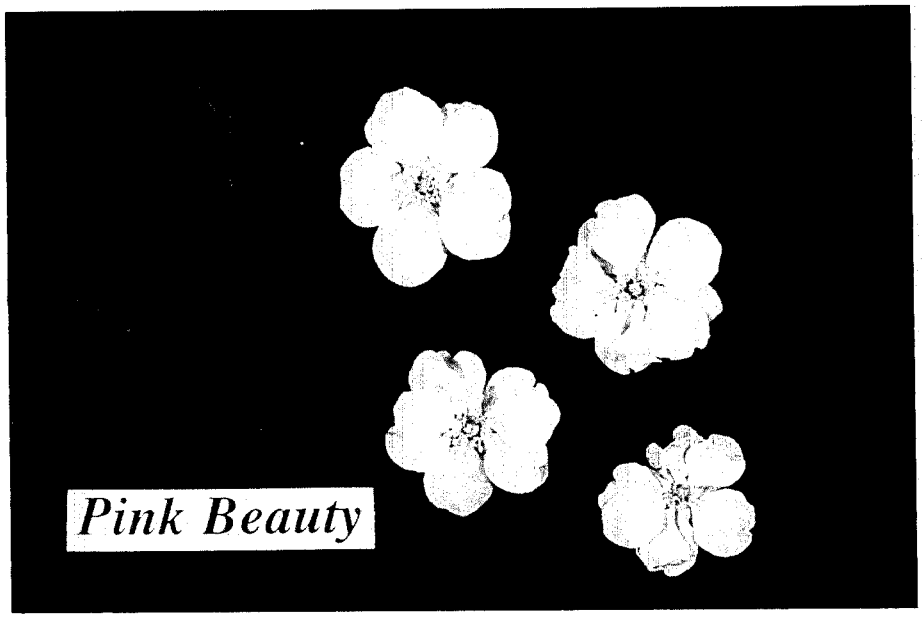
FIG. 3 illustrates a closer view of typical flowers and foliage of the 'Pink Beauty' cultivar when removed from the plant.
Figure 4:
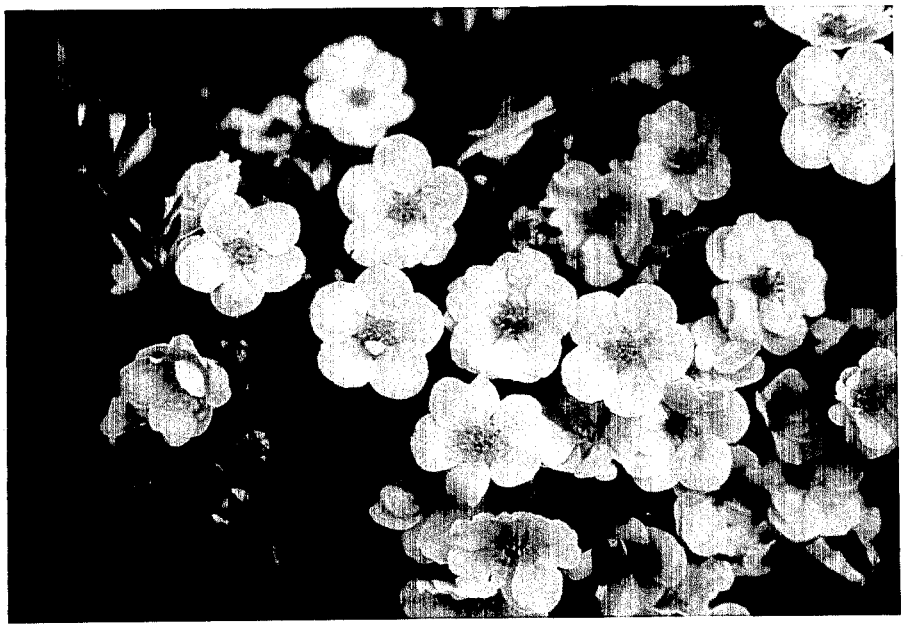

FIG. 4 also illustrates a closer view of typical flowers and foliage of the 'Pink Beauty' cultivar when present on the plant. The intense pink flower coloration of the new cultivar is depicted. Such intense pink coloration is particularly exhibited by the new cultivar when cooler temperatures are experienced during the bud development stage.

DETAILED DESCRIPTION

The following description is based on observation of test plantings of five-year-old plants of the new 'Pink Beauty' cultivar at the University of Manitoba, Winnipeg, Manitoba, Canada. Color terms are presented with reference to The R.H.S. Colour Chart of the Royal Horticultural Society, London, England. General color terms are to be accorded their ordinary dictionary significance.

In the following Table, the new cultivar is compared using average size dimensions to the 'Goldfinger' cultivar and 'Pink Whisper' cultivar when plants of approximately the same age are grown at the same location under the same growing conditions.

| | 'Pink Beauty' | 'Gold-finger' | 'Pink Whisper' |
|---|---|---|---|
| Plant height (cm) | 72 | 96 | 63 |
| Plant width (cm) | 139 | 160 | 118 |
| Leaf length (cm) | 2.2 | 2.8 | 2.0 |
| Leaf width (cm) | 2.3 | 2.9 | 2.1 |
| Corolla: diameter (cm) | 2.6 | 3.5 | 2.4 |
| Corolla: petal width (cm) | 1.1 | 1.5 | 1.0 |
| Corolla: upper surface | Red Group 54B | Yellow Group 12A | Red Group 55C |
| Corolla: under surface | Red Group 36B | Yellow Group 12A | Orange Group 27B |

It will be noted that in addition to the distinctive blossom coloration, the 'Pink Beauty' cultivar commonly exhibits an average plant height, plant width, leaf length, leaf width, corolla diameter, and petal width that is intermediate that of the 'Goldfinger' and 'Pink Whisper' cultivars.

'Pink Beauty' is a vigorous pink-flowering *Potentilla fruticosa* that produces a profusion of flowers over an extended flowering period that generally extends from the summer to the time of the first frost. The semi-double flowers are medium-sized in corolla diameter and petal width. The flower cluster is solitary or cymose. The number of flowering shoots per plant is dense (as illustrated). The color of the stamens is yellow at early maturity and brown at late maturity. The stamens are medium in length. The width of the calyx bracts is substantially equal to the sepal width. The length of the calyx bracts tends to be slightly longer than the sepal length. The pinnately compound leaves are elliptic-oblong in configuration with an entire margin, and are medium in length and width. The mature leaf tends to retain a dark green coloration (as illustrated) even through much of the autumn.

The stem color is medium brown, and is medium in thickness with a small amount of pubescence. The branching is semi-upright and the plant texture is medium both when in leaf and when in winter twig. The plant size is medium in height and width. The plant is hardy to Zone No. 2 of the U.S. plant hardiness map. It also can be grown to advantage in Zone Nos. 3 to 7.

I claim:

1. A new and distinctive cultivar of *Potentilla fruticosa* plant, substantially as herein shown and described, which:

(a) forms in profusion attractive deep pink flowers substantially continuously from summer until frost,
(b) exhibits a medium-sized compact round and spreading growth habit that tends to hold its foliage well even at the base of the plant,
(c) grows satisfactorily even under hot and dry growing conditions where other pink-flowered cultivars of the same species have tended to perform poorly, and
(d) forms attractive deep green foliage.

* * * * *